United States Patent
Luettgen et al.

(10) Patent No.: US 10,561,480 B2
(45) Date of Patent: Feb. 18, 2020

(54) LOAD SENSING FOR ORAL DEVICES

(71) Applicant: WATER PIK, INC., Fort Collins, CO (US)

(72) Inventors: Harold A. Luettgen, Windsor, CO (US); John Fiers, Fort Collins, CO (US); Brian R. Williams, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 306 days.

(21) Appl. No.: 15/588,842

(22) Filed: May 8, 2017

(65) Prior Publication Data

US 2017/0319311 A1 Nov. 9, 2017

Related U.S. Application Data

(60) Provisional application No. 62/333,679, filed on May 9, 2016.

(51) Int. Cl.
*A61C 17/22* (2006.01)

(52) U.S. Cl.
CPC .................. *A61C 17/221* (2013.01)

(58) Field of Classification Search
CPC ..... A61C 17/221; A61C 17/22; A61C 17/225; A61C 17/26; A61C 17/24; A61C 17/3418; A61C 17/3436; A46B 15/0012; A46B 15/0004; A46B 15/0008; A46B 15/0044

See application file for complete search history.

(56) References Cited

U.S. PATENT DOCUMENTS

| | | |
|---|---|---|
| 669,402 A | 3/1901 | Rose |
| 684,951 A | 10/1901 | Rothkranz |
| 914,501 A | 3/1909 | McEachern |
| 933,718 A | 9/1909 | Mahoney |

(Continued)

FOREIGN PATENT DOCUMENTS

| | | |
|---|---|---|
| CH | 435553 | 10/1967 |
| CH | 609238 | 2/1979 |

(Continued)

OTHER PUBLICATIONS

Sonex International: Brushing with the Ultima—The World's Only Dual-Frequency Ultrasonic Toothbrush, Jul. 28, 1999, published at Sonipic.com.

(Continued)

*Primary Examiner* — Shay Karls
(74) *Attorney, Agent, or Firm* — Dorsey & Whitney LLP (57) ABSTRACT

A toothbrush is disclosed. The toothbrush includes a handle, a brush tip connected to the handle, wherein the brush tip includes a plurality of bristles operably connected thereto, a power source, a direct current motor in selective electrical communication with the power source, wherein the motor includes a drive shaft, a drive assembly connected between the brush tip and the drive shaft, wherein the drive assembly converts rotation of the drive shaft into movement of the plurality of bristles, and a control assembly in electrical communication with the motor and the power source; wherein during operation of the motor, the control assembly monitors a current draw by the motor and adjusts a current applied to the direct current motor based on the current draw.

20 Claims, 5 Drawing Sheets

(56) References Cited

U.S. PATENT DOCUMENTS

| | | |
|---|---|---|
| 958,371 A | 5/1910 | Danek |
| 1,018,927 A | 2/1912 | Sarrazin |
| 1,033,819 A | 7/1912 | McMann |
| 1,059,426 A | 4/1913 | Barnes |
| D45,199 S | 2/1914 | McDonagh et al. |
| D45,572 S | 4/1914 | Sarrazin |
| 1,128,139 A | 2/1915 | Hoffman |
| D49,472 S | 8/1916 | Dierke |
| 1,251,250 A | 12/1917 | Libby |
| 1,268,544 A | 6/1918 | Cates |
| 1,278,225 A | 9/1918 | Schamberg |
| 1,296,067 A | 3/1919 | Fuller |
| D53,453 S | 7/1919 | Lloyd |
| 1,313,490 A | 8/1919 | Larson |
| 1,337,173 A | 4/1920 | White |
| 1,355,037 A | 10/1920 | Dziuk |
| D57,327 S | 3/1921 | Gibson |
| 1,382,681 A | 6/1921 | Segal |
| 1,424,879 A | 8/1922 | Carlstedt |
| 1,440,785 A | 1/1923 | Levis |
| 1,456,535 A | 5/1923 | Cartwright |
| 1,488,214 A | 3/1924 | Mason |
| 1,494,448 A | 5/1924 | Sookne |
| 1,497,495 A | 6/1924 | Fincke |
| 1,517,320 A | 12/1924 | Stoddart |
| 1,527,853 A | 2/1925 | Ferdon |
| 1,588,785 A | 6/1926 | Van Sant |
| 1,639,880 A | 8/1927 | Butler |
| 1,657,450 A | 1/1928 | Barnes |
| 1,676,703 A | 7/1928 | Nuyts |
| 1,696,835 A | 12/1928 | Burnett |
| 1,703,642 A | 2/1929 | Sticht |
| 1,794,711 A | 3/1931 | Jacobs |
| 1,796,641 A | 3/1931 | Zimmerman et al. |
| 1,800,993 A | 4/1931 | Funk |
| 1,832,519 A | 11/1931 | Wheat et al. |
| 1,880,617 A | 10/1932 | White |
| 1,916,641 A | 7/1933 | Seeliger |
| 1,927,365 A | 9/1933 | Frolio |
| 1,943,225 A | 1/1934 | McIntyre |
| 1,992,770 A | 2/1935 | Rathbun |
| 2,016,597 A | 10/1935 | Drake |
| 2,016,644 A | 10/1935 | Luball |
| 2,042,239 A | 5/1936 | Planding |
| 2,044,863 A | 6/1936 | Sticht |
| D101,080 S | 9/1936 | Cosad |
| 2,114,947 A | 4/1938 | Warsaw |
| D113,743 S | 3/1939 | Kahn |
| D113,744 S | 3/1939 | Kahn |
| 2,158,738 A | 5/1939 | Baker et al. |
| 2,168,964 A | 8/1939 | Strasser |
| 2,206,726 A | 7/1940 | Lasater |
| 2,209,173 A | 7/1940 | Russell |
| 2,218,072 A | 10/1940 | Runnels |
| 2,226,663 A | 12/1940 | Hill et al. |
| 2,244,098 A | 6/1941 | Busick |
| 2,246,523 A | 6/1941 | Kulik |
| 2,273,717 A | 2/1942 | Millard et al. |
| 2,278,365 A | 3/1942 | Daniels |
| 2,279,355 A | 4/1942 | Wilensky |
| 2,282,700 A | 5/1942 | Bobbroff |
| 2,312,828 A | 3/1943 | Adamsson |
| D136,156 S | 8/1943 | Fuller |
| D139,532 S | 11/1944 | Trecek |
| D141,350 S | 5/1945 | Alexander et al. |
| D144,163 S | 3/1946 | Dolnick |
| 2,401,186 A | 5/1946 | Price |
| 2,405,029 A | 7/1946 | Gallanty et al. |
| D146,271 S | 1/1947 | Stavely |
| 2,414,775 A | 1/1947 | Stavely |
| 2,429,740 A | 10/1947 | Aufsesser |
| 2,450,635 A | 10/1948 | Dembenski |
| D154,598 S | 7/1949 | Gass |
| D155,668 S | 10/1949 | Zandberg et al. |
| D157,669 S | 3/1950 | Graves, Jr. |
| D160,101 S | 9/1950 | MacDonald |
| 2,533,345 A | 12/1950 | Bennett |
| 2,543,999 A | 3/1951 | Voss |
| D163,707 S | 6/1951 | Pifer |
| 2,558,332 A | 6/1951 | Artale |
| 2,567,080 A | 9/1951 | Pifer |
| 2,577,597 A | 12/1951 | Wright et al. |
| 2,583,750 A | 1/1952 | Runnels |
| 2,598,275 A | 5/1952 | Lakin |
| 2,618,003 A | 11/1952 | Robey |
| D169,131 S | 3/1953 | Fay |
| 2,651,068 A | 9/1953 | Seko |
| D170,680 S | 10/1953 | Del Mas |
| D172,693 S | 7/1954 | Wibbelsman et al. |
| D173,616 S | 12/1954 | Hernandez |
| 2,705,335 A | 4/1955 | Glassman et al. |
| 2,709,227 A | 5/1955 | Foley et al. |
| 2,722,703 A | 11/1955 | Green |
| 2,728,928 A | 1/1956 | Beeren |
| 2,734,139 A | 2/1956 | Murphy |
| 2,806,235 A | 9/1957 | Carstairs et al. |
| 2,819,482 A | 1/1958 | Applegate |
| 2,868,215 A | 1/1959 | Mechem |
| 2,875,458 A | 3/1959 | Tsuda |
| 2,917,758 A | 12/1959 | Held et al. |
| 2,931,371 A | 4/1960 | Petitta |
| 2,946,072 A | 7/1960 | Filler et al. |
| 2,962,033 A | 11/1960 | Lew |
| 2,977,614 A | 4/1961 | Demanuele |
| 2,977,682 A | 4/1961 | Flatray |
| 3,103,027 A | 9/1963 | Birch |
| 3,104,405 A | 9/1963 | Perrinjaquet |
| 3,106,216 A | 10/1963 | Kirby |
| D197,048 S | 12/1963 | Troy |
| D197,208 S | 12/1963 | Cassidy et al. |
| 3,143,697 A | 8/1964 | Springer |
| 3,145,404 A | 8/1964 | Fiedler |
| D199,560 S | 11/1964 | Thompson |
| D199,893 S | 12/1964 | Bond et al. |
| 3,159,859 A | 12/1964 | Rasmussen |
| 3,160,902 A | 12/1964 | Aymar |
| 3,168,834 A | 2/1965 | Smithson |
| 3,181,189 A | 5/1965 | Leyden |
| 3,183,538 A | 5/1965 | Hubner |
| 3,195,537 A | 7/1965 | Blasi |
| D202,873 S | 11/1965 | Husted |
| 3,220,039 A | 11/1965 | Dayton et al. |
| 3,229,318 A | 1/1966 | Clemens |
| 3,230,562 A | 1/1966 | Birch |
| D204,127 S | 3/1966 | Syvertson |
| 3,258,805 A | 7/1966 | Rossnan |
| 3,270,416 A | 9/1966 | Massa |
| 3,278,963 A | 10/1966 | Bond |
| 3,289,681 A | 12/1966 | Chambers |
| 3,311,116 A | 3/1967 | Foster |
| 3,316,576 A | 5/1967 | Urbrush |
| 3,335,443 A | 8/1967 | Parisi et al. |
| 3,346,748 A | 10/1967 | McNair |
| 3,358,309 A | 12/1967 | Richardson |
| 3,358,314 A | 12/1967 | Matibag |
| 3,359,588 A | 12/1967 | Kobler |
| 3,364,576 A | 1/1968 | Kern, Jr. |
| D210,066 S | 2/1968 | Johnson |
| 3,369,265 A | 2/1968 | Halberstadt et al. |
| 3,371,260 A | 2/1968 | Jackson et al. |
| D210,349 S | 3/1968 | Boldt |
| 3,375,820 A | 4/1968 | Kuris et al. |
| 3,394,277 A | 7/1968 | Satkunas et al. |
| D212,208 S | 9/1968 | Rogers |
| 3,418,552 A | 12/1968 | Holmes |
| 3,421,524 A | 1/1969 | Waters |
| 3,430,279 A | 3/1969 | Hintze |
| 3,463,994 A | 8/1969 | Spohr |
| 3,466,689 A | 9/1969 | Aurelio et al. |
| 3,472,045 A | 10/1969 | Nelsen et al. |
| 3,472,247 A | 10/1969 | Borsum et al. |
| 3,474,799 A | 10/1969 | Cappello |
| 3,509,874 A | 5/1970 | Stillman |
| 3,535,726 A | 10/1970 | Sawyer |

(56) References Cited

U.S. PATENT DOCUMENTS

| | | |
|---|---|---|
| 3,536,065 A | 10/1970 | Moret |
| 3,538,359 A | 11/1970 | Barowski |
| 3,552,022 A | 1/1971 | Axelsson |
| 3,559,292 A | 2/1971 | Weissman |
| 3,563,233 A | 2/1971 | Bodine |
| 3,588,936 A | 6/1971 | Duve |
| 3,590,814 A | 7/1971 | Bennett et al. |
| D221,823 S | 9/1971 | Cook |
| 3,608,548 A | 9/1971 | Lewis |
| 3,642,344 A | 2/1972 | Corker |
| 3,651,576 A | 3/1972 | Massa |
| 3,660,902 A | 5/1972 | Axelsson |
| 3,667,483 A | 6/1972 | McCabe |
| 3,672,378 A | 6/1972 | Silverman |
| 3,676,218 A | 7/1972 | Sawyer |
| 3,685,080 A | 8/1972 | Hubner |
| 3,722,020 A | 3/1973 | Hills |
| 3,742,549 A | 7/1973 | Scopp et al. |
| 3,759,274 A | 9/1973 | Warner |
| 3,760,799 A | 9/1973 | Crowson |
| 3,792,504 A | 2/1974 | Smith |
| 3,809,977 A | 5/1974 | Balamuth et al. |
| 3,831,611 A | 8/1974 | Hendricks |
| 3,840,932 A | 10/1974 | Balamuth et al. |
| 3,847,167 A | 11/1974 | Brien |
| 3,851,984 A | 12/1974 | Crippa |
| D234,518 S | 3/1975 | Gerlich |
| 3,882,364 A | 5/1975 | Wright et al. |
| 3,902,510 A | 9/1975 | Roth |
| 3,903,601 A | 9/1975 | Anderson et al. |
| 3,939,599 A | 2/1976 | Henry et al. |
| 3,967,617 A | 7/1976 | Krolik |
| 3,973,558 A | 8/1976 | Stouffer et al. |
| 3,977,084 A | 8/1976 | Sloan |
| 3,978,852 A | 9/1976 | Annoni |
| 3,980,906 A | 9/1976 | Kuris et al. |
| 4,004,344 A | 1/1977 | Gold et al. |
| 4,005,722 A | 2/1977 | Bragg |
| 4,008,728 A | 2/1977 | Sanchez |
| 4,010,509 A | 3/1977 | Huish |
| 4,014,354 A | 3/1977 | Garrett |
| 4,019,522 A | 4/1977 | Elbreder |
| 4,033,008 A | 7/1977 | Warren et al. |
| 4,048,723 A | 9/1977 | Thorup |
| 4,051,571 A | 10/1977 | Ayers |
| 4,064,883 A | 12/1977 | Oldham |
| 4,133,339 A | 1/1979 | Naslund |
| 4,141,352 A | 2/1979 | Ebner et al. |
| 4,156,620 A | 5/1979 | Clemens |
| 4,177,434 A | 12/1979 | Ida |
| D254,162 S | 2/1980 | Barker |
| 4,192,035 A | 3/1980 | Kuris |
| 4,203,431 A | 5/1980 | Abura et al. |
| 4,205,664 A | 6/1980 | Baccialon |
| 4,219,619 A | 8/1980 | Zarow |
| 4,235,253 A | 11/1980 | Moore |
| 4,245,658 A | 1/1981 | Lecouturier |
| RE30,536 E | 3/1981 | Perdreaux, Jr. |
| 4,255,693 A | 3/1981 | Keidl |
| 4,265,257 A | 5/1981 | Salyer |
| 4,268,933 A | 5/1981 | Papas |
| 4,271,382 A | 6/1981 | Maeda et al. |
| 4,271,384 A | 6/1981 | Beiling et al. |
| 4,271,854 A | 6/1981 | Bengtsson |
| 4,275,363 A | 6/1981 | Mishiro et al. |
| 4,288,883 A | 9/1981 | Dolinsky |
| 4,289,486 A | 9/1981 | Sargeant |
| 4,303,064 A | 12/1981 | Buffa |
| 4,307,740 A | 12/1981 | Florindez et al. |
| 4,319,377 A | 3/1982 | Tarrson et al. |
| 4,319,595 A | 3/1982 | Ulrich |
| 4,326,547 A | 4/1982 | Verplank |
| 4,326,548 A | 4/1982 | Wagner |
| 4,326,549 A | 4/1982 | Hinding |
| 4,331,422 A | 5/1982 | Heyman |
| 4,333,197 A | 6/1982 | Kuris |
| 4,336,622 A | 6/1982 | Teague, Jr. et al. |
| D265,515 S | 7/1982 | Levine |
| 4,338,957 A | 7/1982 | Meibauer |
| D265,698 S | 8/1982 | Roth |
| 4,346,492 A | 8/1982 | Solow |
| 4,347,839 A | 9/1982 | Youngclaus, Jr. |
| 4,353,141 A | 10/1982 | Teague, Jr. et al. |
| 4,356,585 A | 11/1982 | Protell et al. |
| 4,381,478 A | 4/1983 | Saijo et al. |
| 4,395,665 A | 7/1983 | Buchas |
| 4,397,327 A | 8/1983 | Hadary |
| D270,972 S | 10/1983 | Rosofsky |
| D272,565 S | 2/1984 | Levine |
| D272,680 S | 2/1984 | Stocchi |
| 4,429,997 A | 2/1984 | Matthews |
| 4,432,729 A | 2/1984 | Fattaleh |
| 4,434,806 A | 3/1984 | Givens |
| 4,442,830 A | 4/1984 | Markau |
| D274,018 S | 5/1984 | Usui |
| 4,450,599 A | 5/1984 | Scheller et al. |
| 4,455,704 A | 6/1984 | Williams |
| 4,458,702 A | 7/1984 | Grollimund |
| 4,488,327 A | 12/1984 | Snider |
| 4,490,114 A | 12/1984 | Kleesattel |
| 4,505,678 A | 3/1985 | Andersson |
| 4,517,701 A | 5/1985 | Stanford, Jr. |
| 4,519,111 A | 5/1985 | Cavazza |
| 4,522,355 A | 6/1985 | Moran |
| 4,522,595 A | 6/1985 | Selvidge |
| 4,543,679 A | 10/1985 | Rosofsky et al. |
| D281,202 S | 11/1985 | Thompson |
| 4,562,413 A | 12/1985 | Mishiro et al. |
| 4,564,794 A | 1/1986 | Kilen et al. |
| 4,571,768 A | 2/1986 | Kawashima |
| 4,576,190 A | 3/1986 | Youssef |
| 4,577,649 A | 3/1986 | Shimenkov |
| 4,578,033 A | 3/1986 | Mossle et al. |
| D283,374 S | 4/1986 | Cheuk-Yiu |
| 4,585,415 A | 4/1986 | Hommann |
| 4,586,521 A | 5/1986 | Urso |
| D284,236 S | 6/1986 | Collet |
| D284,528 S | 7/1986 | Jurado |
| 4,603,448 A * | 8/1986 | Middleton ............. A61C 17/26 15/22.1 |
| 4,605,025 A | 8/1986 | McSpadden |
| 4,608,019 A | 8/1986 | Kumabe et al. |
| 4,610,043 A | 9/1986 | Vezjak |
| 4,617,695 A | 10/1986 | Amos et al. |
| 4,617,718 A | 10/1986 | Andersson |
| 4,619,009 A | 10/1986 | Rosenstatter |
| D287,073 S | 12/1986 | Thompson |
| 4,634,376 A | 1/1987 | Mossle et al. |
| 4,644,937 A | 2/1987 | Hommann |
| 4,655,198 A | 4/1987 | Hommann |
| 4,672,706 A | 6/1987 | Hill |
| D292,448 S | 10/1987 | Vianello |
| 4,698,869 A | 10/1987 | Mierau et al. |
| 4,706,322 A | 11/1987 | Nicolas |
| 4,706,695 A | 11/1987 | Urso |
| D294,885 S | 3/1988 | Mollenhoff |
| 4,729,142 A | 3/1988 | Yoshioka |
| D297,467 S | 8/1988 | McCann |
| 4,766,630 A | 8/1988 | Hegemann |
| 4,776,054 A | 10/1988 | Rauch |
| 4,787,847 A | 11/1988 | Martin et al. |
| 4,791,940 A | 12/1988 | Hirshfeld et al. |
| 4,800,608 A | 1/1989 | Key |
| 4,802,255 A | 2/1989 | Breuer et al. |
| 4,811,445 A | 3/1989 | Lagieski et al. |
| 4,820,153 A | 4/1989 | Romhild et al. |
| 4,820,154 A | 4/1989 | Romhild et al. |
| 4,827,550 A | 5/1989 | Graham et al. |
| 4,827,551 A | 5/1989 | Maser et al. |
| 4,827,552 A | 5/1989 | Bojar et al. |
| 4,832,063 A | 5/1989 | Smole |
| D301,770 S | 6/1989 | Bethany |
| 4,844,104 A | 7/1989 | Martin |
| 4,845,795 A | 7/1989 | Crawford et al. |

(56) References Cited

U.S. PATENT DOCUMENTS

| | | |
|---|---|---|
| 4,856,133 A | 8/1989 | Sanchez |
| 4,864,676 A | 9/1989 | Schaiper |
| D303,876 S | 10/1989 | Clemens et al. |
| 4,871,396 A | 10/1989 | Tsujita et al. |
| 4,873,496 A | 10/1989 | Ohgihara et al. |
| 4,875,265 A | 10/1989 | Yoshida |
| 4,877,934 A | 10/1989 | Spinello |
| 4,879,781 A | 11/1989 | Desimone |
| 4,880,382 A | 11/1989 | Moret et al. |
| 4,887,052 A | 12/1989 | Murakami et al. |
| 4,892,191 A | 1/1990 | Nakamara |
| 4,908,902 A | 3/1990 | McNab et al. |
| 4,913,133 A | 4/1990 | Tichy |
| 4,913,176 A | 4/1990 | DeNiro |
| 4,922,936 A | 5/1990 | Buzzi et al. |
| D308,765 S | 6/1990 | Johnson |
| 4,974,278 A | 12/1990 | Hommann |
| 4,984,173 A | 1/1991 | Imam et al. |
| 4,989,287 A | 2/1991 | Scherer |
| 4,991,249 A | 2/1991 | Suroff |
| 4,995,403 A | 2/1991 | Beckman et al. |
| 5,000,684 A | 3/1991 | Odrich |
| 5,002,487 A | 3/1991 | Tichy |
| 5,007,127 A | 4/1991 | Paolo |
| 5,016,660 A | 5/1991 | Boggs |
| 5,020,179 A | 6/1991 | Scherer |
| 5,033,150 A | 7/1991 | Gross et al. |
| D318,918 S | 8/1991 | Hartwein |
| D319,363 S | 8/1991 | Uemura et al. |
| 5,046,212 A | 9/1991 | O'Conke |
| 5,050,625 A | 9/1991 | Siekmann |
| 5,054,149 A | 10/1991 | Si-Hoe et al. |
| D321,285 S | 11/1991 | Hirabayashi |
| 5,062,797 A | 11/1991 | Gonser |
| 5,067,223 A | 11/1991 | Bruno |
| D321,986 S | 12/1991 | Snyder et al. |
| 5,068,939 A | 12/1991 | Holland |
| 5,069,233 A | 12/1991 | Ritter |
| 5,069,621 A | 12/1991 | Paradis |
| 5,071,348 A | 12/1991 | Woog |
| 5,072,477 A | 12/1991 | Pai |
| 5,072,482 A | 12/1991 | Bojar et al. |
| 5,077,855 A | 1/1992 | Ambasz |
| 5,085,236 A | 2/1992 | Odneal et al. |
| 5,088,145 A | 2/1992 | Whitefield |
| D324,957 S | 3/1992 | Piano |
| 5,094,256 A | 3/1992 | Barth |
| 5,095,470 A | 3/1992 | Oka et al. |
| 5,100,321 A | 3/1992 | Coss et al. |
| 5,120,225 A | 6/1992 | Amit |
| 5,123,841 A | 6/1992 | Millner |
| 5,125,837 A | 6/1992 | Warrin et al. |
| 5,133,661 A | 7/1992 | Euvrard |
| 5,138,733 A | 8/1992 | Bock |
| 5,145,369 A | 9/1992 | Lustig et al. |
| 5,146,643 A | 9/1992 | Bojar et al. |
| 5,150,492 A | 9/1992 | Suroff |
| 5,151,030 A | 9/1992 | Comeaux |
| D330,116 S | 10/1992 | Crawford et al. |
| D330,286 S | 10/1992 | Curtis et al. |
| D330,458 S | 10/1992 | Curtis et al. |
| 5,152,394 A | 10/1992 | Hughes |
| 5,163,375 A | 11/1992 | Withers et al. |
| 5,165,131 A | 11/1992 | Suroff |
| 5,167,193 A | 12/1992 | Withers et al. |
| 5,169,313 A | 12/1992 | Kline |
| 5,170,809 A | 12/1992 | Imai et al. |
| 5,174,314 A | 12/1992 | Charatan |
| 5,176,157 A | 1/1993 | Mazza |
| 5,177,826 A | 1/1993 | Vrignaud et al. |
| 5,180,363 A | 1/1993 | Idemoto et al. |
| D332,873 S | 2/1993 | Hall |
| 5,183,063 A | 2/1993 | Ringle et al. |
| 5,183,156 A | 2/1993 | Bruno |
| 5,184,368 A | 2/1993 | Holland |
| 5,184,632 A | 2/1993 | Gross et al. |
| 5,186,191 A | 2/1993 | Loubier |
| 5,188,133 A | 2/1993 | Romanus |
| 5,189,751 A | 3/1993 | Giuliani et al. |
| 5,193,678 A | 3/1993 | Janocik et al. |
| 5,198,732 A | 3/1993 | Morimoto |
| D334,472 S | 4/1993 | Curtis et al. |
| 5,201,092 A | 4/1993 | Colson |
| D335,579 S | 5/1993 | Chuang |
| 5,207,773 A | 5/1993 | Henderson |
| 5,213,434 A | 5/1993 | Hahn |
| 5,214,819 A | 6/1993 | Kirchner |
| 5,217,031 A | 6/1993 | Santoro |
| 5,224,500 A | 7/1993 | Stella |
| 5,226,206 A | 7/1993 | Davidovitz et al. |
| 5,236,358 A | 8/1993 | Sieffert |
| 5,245,117 A | 9/1993 | Withers et al. |
| 5,246,022 A | 9/1993 | Israel et al. |
| 5,247,716 A | 9/1993 | Bock |
| 5,253,382 A | 10/1993 | Beny |
| 5,261,430 A | 11/1993 | Mochel |
| 5,263,218 A | 11/1993 | Giuliani et al. |
| D341,943 S | 12/1993 | Si-Hoe |
| D342,160 S | 12/1993 | Curtis et al. |
| D342,161 S | 12/1993 | Curtis et al. |
| D342,162 S | 12/1993 | Curtis et al. |
| 5,267,579 A | 12/1993 | Bushberger |
| D343,064 S | 1/1994 | Reno |
| 5,279,314 A | 1/1994 | Poulos et al. |
| 5,289,604 A | 3/1994 | Kressner |
| 5,293,886 A | 3/1994 | Czapor |
| 5,294,896 A | 3/1994 | Kjellander et al. |
| D346,212 S | 4/1994 | Hosl |
| 5,299,723 A | 4/1994 | Hempel |
| 5,301,381 A | 4/1994 | Klupt |
| 5,305,492 A | 4/1994 | Giuliani et al. |
| D346,697 S | 5/1994 | O'Conke |
| 5,309,590 A | 5/1994 | Giuliani et al. |
| 5,309,591 A | 5/1994 | Hägele et al. |
| 5,311,632 A | 5/1994 | Center |
| 5,311,633 A | 5/1994 | Herzog et al. |
| 5,315,731 A | 5/1994 | Millar |
| D347,943 S | 6/1994 | Perry |
| 5,323,796 A | 6/1994 | Urso |
| 5,335,389 A | 8/1994 | Curtis et al. |
| 5,337,435 A | 8/1994 | Krasner et al. |
| 5,339,482 A | 8/1994 | Desimone et al. |
| 5,341,534 A | 8/1994 | Serbinski et al. |
| 5,341,537 A | 8/1994 | Curtis et al. |
| 5,351,358 A | 10/1994 | Larrimore |
| 5,353,460 A | 10/1994 | Bauman |
| 5,354,246 A | 10/1994 | Gotman |
| 5,355,638 A | 10/1994 | Hoffman |
| 5,358,328 A | 10/1994 | Inoue et al. |
| D352,396 S | 11/1994 | Curtis et al. |
| D352,829 S | 11/1994 | Perry |
| 5,359,747 A | 11/1994 | Amakasu |
| 5,365,627 A | 11/1994 | Jousson et al. |
| D353,490 S | 12/1994 | Hartwein |
| 5,369,831 A | 12/1994 | Bock |
| 5,371,915 A | 12/1994 | Key |
| 5,373,602 A | 12/1994 | Bang |
| D354,168 S | 1/1995 | Hartwein |
| 5,378,153 A | 1/1995 | Giuliani et al. |
| 5,383,242 A | 1/1995 | Bigler et al. |
| 5,392,483 A | 2/1995 | Heinzelman et al. |
| 5,393,229 A | 2/1995 | Ram |
| 5,396,678 A | 3/1995 | Bredall et al. |
| 5,398,368 A | 3/1995 | Elder |
| 5,400,811 A | 3/1995 | Meibauer |
| 5,404,608 A | 4/1995 | Hommann |
| 5,406,664 A | 4/1995 | Hukuba |
| 5,406,965 A | 4/1995 | Levine |
| D358,486 S | 5/1995 | Loew |
| D358,713 S | 5/1995 | Perry |
| D358,801 S | 5/1995 | Vos |
| 5,411,041 A | 5/1995 | Ritter |
| 5,412,827 A | 5/1995 | Muller et al. |
| 5,416,942 A | 5/1995 | Baldacci et al. |

(56) References Cited

U.S. PATENT DOCUMENTS

| | | |
|---|---|---|
| 5,419,346 A | 5/1995 | Tipp |
| 5,419,703 A | 5/1995 | Warrin et al. |
| D358,938 S | 6/1995 | Schneider et al. |
| 5,421,726 A | 6/1995 | Okada |
| 5,435,032 A | 7/1995 | McDougall |
| 5,438,726 A | 8/1995 | Leite |
| 5,446,940 A | 9/1995 | Curtis et al. |
| D363,605 S | 10/1995 | Kou et al. |
| 5,459,898 A | 10/1995 | Bacolot |
| 5,461,744 A | 10/1995 | Merbach |
| 5,467,494 A | 11/1995 | Muller et al. |
| 5,467,495 A | 11/1995 | Boland et al. |
| 5,482,466 A | 1/1996 | Haynes |
| 5,484,281 A | 1/1996 | Renow et al. |
| 5,496,256 A | 3/1996 | Bock et al. |
| 5,499,420 A | 3/1996 | Boland |
| 5,504,958 A | 4/1996 | Herzog |
| 5,504,959 A | 4/1996 | Yukawa et al. |
| 5,511,270 A | 4/1996 | Eliachar et al. |
| 5,511,275 A | 4/1996 | Volpenhein et al. |
| D370,125 S | 5/1996 | Craft et al. |
| 5,518,012 A | 5/1996 | Dolan et al. |
| D370,347 S | 6/1996 | Heinzelman et al. |
| 5,529,494 A | 6/1996 | Vlacancich |
| D371,242 S | 7/1996 | Shimatsu et al. |
| 5,530,981 A | 7/1996 | Chen |
| 5,544,382 A | 8/1996 | Giuliani et al. |
| 5,545,968 A | 8/1996 | Hilfinger et al. |
| 5,546,624 A | 8/1996 | Bock |
| 5,546,626 A | 8/1996 | Chung |
| 5,561,881 A | 10/1996 | Klinger et al. |
| D375,841 S | 11/1996 | Serbinski |
| 5,573,020 A | 11/1996 | Robinson |
| 5,577,285 A | 11/1996 | Drossler |
| D376,695 S | 12/1996 | Tveras |
| 5,579,786 A | 12/1996 | Wolk et al. |
| 5,584,690 A | 12/1996 | Maassarani |
| 5,588,452 A | 12/1996 | Peck |
| 5,606,984 A | 3/1997 | Gao |
| 5,609,170 A | 3/1997 | Roth |
| 5,613,258 A | 3/1997 | Hilfinger et al. |
| 5,613,259 A | 3/1997 | Craft et al. |
| 5,617,601 A | 4/1997 | McDougall |
| 5,617,602 A | 4/1997 | Okada |
| 5,618,275 A | 4/1997 | Bock |
| 5,619,766 A | 4/1997 | Zhadanov et al. |
| 5,623,746 A | 4/1997 | Ichiro |
| 5,625,916 A | 5/1997 | McDougall |
| 5,628,082 A | 5/1997 | Moskovich |
| D380,903 S | 7/1997 | Moskovich |
| D381,468 S | 7/1997 | Dolan et al. |
| 5,651,157 A | 7/1997 | Hahn |
| D382,407 S | 8/1997 | Craft et al. |
| 5,652,990 A | 8/1997 | Driesen et al. |
| 5,653,591 A | 8/1997 | Loge |
| 5,678,274 A | 10/1997 | Liu |
| 5,678,578 A | 10/1997 | Kossak et al. |
| D386,314 S | 11/1997 | Moskovich |
| 5,687,446 A | 11/1997 | Chen et al. |
| 5,697,117 A | 12/1997 | Craft |
| 5,700,146 A | 12/1997 | Kucar |
| RE35,712 E | 1/1998 | Murayama |
| 5,704,087 A | 1/1998 | Strub |
| 5,709,233 A | 1/1998 | Boland et al. |
| 5,718,667 A | 2/1998 | Sugimoto et al. |
| 5,732,433 A | 3/1998 | Göcking et al. |
| 5,735,011 A | 4/1998 | Asher |
| 5,738,575 A | 4/1998 | Bock |
| 5,742,972 A | 4/1998 | Bredall et al. |
| 5,749,380 A | 5/1998 | Zebuhr |
| 5,762,078 A | 6/1998 | Zebuhr |
| 5,775,346 A | 7/1998 | Szyszkowski |
| 5,784,742 A * | 7/1998 | Giuliani ............ A46B 15/0002 15/167.1 |
| 5,784,743 A | 7/1998 | Shek |
| D397,251 S | 8/1998 | Eguchi et al. |
| D397,254 S | 8/1998 | Moskovich |
| 5,787,908 A | 8/1998 | Robinson |
| 5,794,295 A | 8/1998 | Shen |
| 5,815,872 A | 10/1998 | Meginnis, III et al. |
| 5,816,271 A | 10/1998 | Urso |
| 5,822,821 A | 10/1998 | Sham |
| 5,827,064 A | 10/1998 | Bock |
| D400,713 S | 11/1998 | Solanki |
| 5,836,030 A | 11/1998 | Hazeu et al. |
| 5,842,244 A | 12/1998 | Hilfinger et al. |
| 5,850,655 A | 12/1998 | Göcking et al. |
| 5,851,514 A | 12/1998 | Hassan et al. |
| D403,511 S | 1/1999 | Serbinski |
| 5,855,216 A | 1/1999 | Robinson |
| 5,862,558 A | 1/1999 | Hilfinger et al. |
| 5,864,911 A | 2/1999 | Arnoux |
| 5,864,915 A | 2/1999 | Ra |
| 5,867,856 A | 2/1999 | Herzog |
| 5,875,797 A | 3/1999 | Chiang et al. |
| 5,893,175 A | 4/1999 | Cooper |
| 5,896,614 A | 4/1999 | Flewitt |
| 5,896,615 A | 4/1999 | Zaksenberg |
| 5,899,693 A | 5/1999 | Himeno et al. |
| 5,900,230 A | 5/1999 | Cutler |
| 5,901,397 A | 5/1999 | Hafele et al. |
| D410,787 S | 6/1999 | Barre et al. |
| 5,908,038 A | 6/1999 | Bennett |
| D411,769 S | 7/1999 | Wright |
| 5,921,254 A | 7/1999 | Carlucci et al. |
| 5,927,300 A | 7/1999 | Boland et al. |
| 5,927,976 A | 7/1999 | Wu |
| 5,930,858 A | 8/1999 | Jung |
| 5,931,170 A | 8/1999 | Wu |
| 5,934,908 A | 8/1999 | Woog et al. |
| 5,943,723 A | 8/1999 | Hilfinger et al. |
| 5,944,033 A | 8/1999 | Robinson |
| D413,694 S | 9/1999 | Bennett |
| D414,937 S | 10/1999 | Cornu et al. |
| D414,939 S | 10/1999 | Pedro, Jr. et al. |
| 5,974,613 A | 11/1999 | Herzog |
| 5,974,615 A | 11/1999 | Schwarz-Hartmann et al. |
| 5,980,541 A | 11/1999 | Tenzer |
| 5,987,681 A | 11/1999 | Hahn et al. |
| 5,991,957 A | 11/1999 | Watanabe |
| D417,960 S | 12/1999 | Moskovich et al. |
| 6,000,083 A | 12/1999 | Blaustein et al. |
| 6,009,589 A | 1/2000 | Driesen et al. |
| 6,021,538 A | 2/2000 | Kressner et al. |
| 6,026,828 A | 2/2000 | Altshuler |
| 6,032,313 A | 3/2000 | Tsang |
| 6,035,476 A | 3/2000 | Underwood et al. |
| 6,047,429 A | 4/2000 | Wu |
| 6,047,711 A | 4/2000 | Wagner |
| 6,050,818 A | 4/2000 | Boland et al. |
| D423,784 S | 5/2000 | Joulin |
| 6,065,176 A | 5/2000 | Watanabe et al. |
| 6,081,957 A | 7/2000 | Webb |
| 6,092,252 A | 7/2000 | Fischer et al. |
| 6,095,811 A | 8/2000 | Stearns |
| 6,102,700 A | 8/2000 | Haczek et al. |
| 6,106,294 A | 8/2000 | Daniel |
| 6,138,310 A | 10/2000 | Porper et al. |
| 6,140,723 A | 10/2000 | Matsui et al. |
| 6,148,462 A | 11/2000 | Zseng |
| D434,563 S | 12/2000 | Lim et al. |
| 6,154,912 A | 12/2000 | Li |
| 6,162,202 A | 12/2000 | Sicurelli et al. |
| 6,164,967 A | 12/2000 | Sale et al. |
| 6,165,131 A | 12/2000 | Cuse et al. |
| D437,090 S | 1/2001 | Lang et al. |
| D437,091 S | 1/2001 | Lang et al. |
| 6,178,579 B1 | 1/2001 | Blaustein et al. |
| D437,663 S | 2/2001 | Lang et al. |
| D437,976 S | 2/2001 | Narayanan et al. |
| D437,977 S | 2/2001 | Lang et al. |
| D438,306 S | 2/2001 | Narayanan |
| 6,183,254 B1 | 2/2001 | Cohen |
| 6,195,828 B1 | 3/2001 | Fritsch |

(56) References Cited

U.S. PATENT DOCUMENTS

| | | |
|---|---|---|
| 6,202,242 B1 | 3/2001 | Salmon et al. |
| 6,203,320 B1 | 3/2001 | Williams et al. |
| 6,220,857 B1 | 4/2001 | Abels |
| 6,230,354 B1 | 5/2001 | Sproat |
| 6,230,717 B1 | 5/2001 | Marx et al. |
| 6,233,773 B1 | 5/2001 | Karge et al. |
| 6,237,178 B1 | 5/2001 | Krammer et al. |
| D444,629 S | 7/2001 | Etter et al. |
| 6,253,404 B1 | 7/2001 | Boland et al. |
| 6,267,593 B1 | 7/2001 | Haczek et al. |
| 6,299,444 B1 | 10/2001 | Cohen |
| 6,308,358 B2 | 10/2001 | Gruber et al. |
| 6,308,359 B2 | 10/2001 | Fritsch et al. |
| 6,341,400 B1 | 1/2002 | Kobayashi et al. |
| 6,343,396 B1 | 2/2002 | Simovitz et al. |
| 6,343,400 B1 | 2/2002 | Massholder et al. |
| 6,347,425 B1 | 2/2002 | Fattori et al. |
| 6,349,442 B1 | 2/2002 | Cohen et al. |
| 6,353,956 B1 | 3/2002 | Berge |
| 6,360,395 B2 | 3/2002 | Blaustein et al. |
| 6,360,398 B1 | 3/2002 | Wiegner et al. |
| 6,363,565 B1 | 4/2002 | Paffrath |
| 6,365,108 B1 | 4/2002 | Philyaw |
| 6,367,108 B1 | 4/2002 | Fritsch et al. |
| 6,374,448 B2 | 4/2002 | Seifert |
| 6,375,459 B1 | 4/2002 | Kamen et al. |
| RE36,699 E | 5/2002 | Murayama |
| 6,381,795 B1 | 5/2002 | Hofmann et al. |
| 6,401,288 B1 | 6/2002 | Porper et al. |
| 6,421,865 B1 | 7/2002 | McDougall |
| 6,421,866 B1 | 7/2002 | McDougall |
| 6,421,867 B1 | 7/2002 | Weihrauch |
| 6,422,867 B2 | 7/2002 | Lang et al. |
| 6,434,773 B1 | 8/2002 | Kuo |
| D463,627 S | 9/2002 | Lang et al. |
| 6,446,294 B1 | 9/2002 | Specht |
| 6,446,295 B1 | 9/2002 | Calabrese |
| 6,447,293 B1 | 9/2002 | Sokol et al. |
| 6,453,497 B1 | 9/2002 | Chiang et al. |
| 6,453,498 B1 | 9/2002 | Wu |
| 6,453,499 B1 | 9/2002 | Leuermann |
| 6,463,615 B1 | 10/2002 | Gruber et al. |
| 6,490,747 B1 | 12/2002 | Metwally |
| 6,497,237 B1 | 12/2002 | Ali |
| 6,510,575 B2 | 1/2003 | Calabrese |
| 6,526,994 B1 | 3/2003 | Santoro |
| 6,536,066 B2 | 3/2003 | Dickie |
| 6,564,940 B2 | 5/2003 | Blaustein et al. |
| 6,571,804 B2 | 6/2003 | Adler |
| 6,574,820 B1 | 6/2003 | DePuydt et al. |
| 6,581,233 B1 | 6/2003 | Cheng |
| 6,581,234 B2 | 6/2003 | Lee et al. |
| 6,588,042 B2 | 7/2003 | Fritsch et al. |
| 6,599,048 B2 | 7/2003 | Kuo |
| 6,609,527 B2 | 8/2003 | Brown |
| 6,609,910 B2 | 8/2003 | Narayanan |
| 6,619,219 B2 | 9/2003 | Marcon et al. |
| 6,622,333 B1 | 9/2003 | Rehkemper et al. |
| 6,647,577 B2 | 11/2003 | Tam |
| D484,311 S | 12/2003 | Cacka et al. |
| 6,654,979 B2 | 12/2003 | Calabrese |
| 6,659,674 B2 | 12/2003 | Carlucci et al. |
| 6,665,901 B2 | 12/2003 | Driesen et al. |
| 6,691,363 B2 | 2/2004 | Huen |
| 6,701,565 B2 | 3/2004 | Hafemann |
| 6,709,185 B2 | 3/2004 | Lefevre |
| 6,721,986 B2 | 4/2004 | Zhuan |
| 6,725,490 B2 | 4/2004 | Blaustein et al. |
| 6,735,803 B2 | 5/2004 | Kuo |
| 6,735,804 B2 | 5/2004 | Carlucci et al. |
| 6,739,012 B2 | 5/2004 | Grez et al. |
| 6,751,823 B2 | 6/2004 | Biro et al. |
| 6,760,945 B2 | 7/2004 | Ferber et al. |
| 6,760,946 B2 | 7/2004 | DePuydt |
| 6,766,548 B1 | 7/2004 | Lukas et al. |
| 6,766,549 B2 | 7/2004 | Klupt |
| 6,766,807 B2 | 7/2004 | Piccolo et al. |
| 6,779,126 B1 | 8/2004 | Lin et al. |
| 6,779,215 B2 | 8/2004 | Hartman et al. |
| 6,785,926 B2 | 9/2004 | Green |
| 6,785,929 B2 | 9/2004 | Fritsch et al. |
| 6,792,640 B2 | 9/2004 | Lev |
| 6,795,993 B2 | 9/2004 | Lin |
| 6,798,169 B2 | 9/2004 | Stratmann et al. |
| 6,799,346 B2 | 10/2004 | Jeng et al. |
| 6,802,097 B2 | 10/2004 | Hafliger et al. |
| 6,810,550 B1 | 11/2004 | Wuelknitz et al. |
| 6,813,793 B2 | 11/2004 | Eliav |
| 6,813,794 B2 | 11/2004 | Weng |
| 6,821,119 B2 | 11/2004 | Shortt et al. |
| 6,823,875 B2 | 11/2004 | Hotta et al. |
| 6,827,910 B2 | 12/2004 | Chen |
| 6,829,801 B2 | 12/2004 | Schutz |
| 6,832,819 B1 | 12/2004 | Weihrauch |
| D500,599 S | 1/2005 | Callaghan |
| D501,084 S | 1/2005 | Schaefer et al. |
| 6,836,917 B2 | 1/2005 | Blaustein et al. |
| 6,845,537 B2 | 1/2005 | Wong |
| 6,848,141 B2 | 2/2005 | Eliav et al. |
| 6,851,150 B2 | 2/2005 | Chiang |
| 6,851,153 B2 | 2/2005 | Lehman |
| 6,854,965 B2 | 2/2005 | Ebner et al. |
| 6,862,771 B1 | 3/2005 | Muller |
| 6,871,373 B2 | 3/2005 | Driesen et al. |
| 6,874,509 B2 | 4/2005 | Bergman |
| 6,886,207 B1 | 5/2005 | Solanki |
| 6,889,401 B2 | 5/2005 | Fattori et al. |
| 6,889,829 B2 | 5/2005 | Lev et al. |
| 6,892,412 B2 | 5/2005 | Gatzemeyer et al. |
| 6,892,413 B2 | 5/2005 | Blaustein et al. |
| 6,895,625 B2 | 5/2005 | Lev et al. |
| 6,895,629 B1 | 5/2005 | Wenzler |
| 6,902,337 B1 | 6/2005 | Kuo |
| 6,907,636 B2 | 6/2005 | Hafemann |
| 6,918,153 B2 | 7/2005 | Gruber |
| 6,920,659 B2 | 7/2005 | Cacka et al. |
| 6,920,660 B2 | 7/2005 | Lam |
| 6,928,685 B1 | 8/2005 | Blaustein et al. |
| 6,931,688 B2 | 8/2005 | Moskovich et al. |
| 6,938,293 B2 | 9/2005 | Eliav et al. |
| 6,938,294 B2 | 9/2005 | Fattori et al. |
| 6,944,901 B2 | 9/2005 | Gatzemeyer et al. |
| 6,945,397 B2 | 9/2005 | Brattesani et al. |
| 6,948,209 B2 | 9/2005 | Chan |
| 6,952,854 B2 | 10/2005 | Blaustein et al. |
| 6,952,855 B2 | 10/2005 | Lev et al. |
| 6,954,961 B2 | 10/2005 | Ferber et al. |
| 6,955,539 B2 | 10/2005 | Shortt et al. |
| 6,957,468 B2 | 10/2005 | Driesen et al. |
| 6,957,469 B2 | 10/2005 | Davies |
| 6,966,093 B2 | 11/2005 | Eliav et al. |
| 6,973,694 B2 | 12/2005 | Schutz et al. |
| 6,983,507 B2 | 1/2006 | McDougall |
| 6,988,777 B2 | 1/2006 | Pfenniger et al. |
| 6,990,706 B2 | 1/2006 | Broecker et al. |
| D515,318 S | 2/2006 | Chan et al. |
| 6,993,803 B2 | 2/2006 | Chan |
| 6,997,191 B2 | 2/2006 | Nudo, Sr. |
| 7,007,331 B2 | 3/2006 | Davics et al. |
| 7,008,225 B2 | 3/2006 | Ito et al. |
| 7,020,925 B1 | 4/2006 | Gitelis |
| 7,021,851 B1 | 4/2006 | King |
| 7,024,717 B2 | 4/2006 | Hilscher et al. |
| 7,024,718 B2 | 4/2006 | Chu |
| 7,036,180 B2 | 5/2006 | Hanlon |
| 7,055,205 B2 | 6/2006 | Aoyama |
| 7,059,334 B2 | 6/2006 | Dougan et al. |
| 7,065,821 B2 | 6/2006 | Fattori |
| RE39,185 E | 7/2006 | Noe et al. |
| 7,070,354 B1 | 7/2006 | Gutierrez-Caro |
| 7,080,980 B2 | 7/2006 | Klupt |
| 7,082,638 B2 | 8/2006 | Koh |
| 7,082,950 B2 | 8/2006 | Kossak et al. |
| 7,086,111 B2 | 8/2006 | Hilscher et al. |

(56) References Cited

U.S. PATENT DOCUMENTS

| | | |
|---|---|---|
| 7,089,621 B2 | 8/2006 | Hohlbein |
| 7,120,960 B2 | 10/2006 | Hilscher et al. |
| 7,122,921 B2 | 10/2006 | Hall et al. |
| 7,124,461 B2 | 10/2006 | Blaustein et al. |
| 7,124,462 B2 | 10/2006 | Lee |
| 7,128,492 B1 | 10/2006 | Thames, Jr. |
| 7,137,136 B1 | 11/2006 | Gatzemeyer et al. |
| 7,140,058 B2 | 11/2006 | Gatzemeyer et al. |
| 7,146,675 B2 | 12/2006 | Ansari et al. |
| 7,162,764 B2 | 1/2007 | Drossler et al. |
| 7,162,767 B2 | 1/2007 | Pfenniger et al. |
| 7,168,122 B1 | 1/2007 | Riddell |
| 7,168,125 B2 | 1/2007 | Hohlbein |
| 7,174,596 B2 | 2/2007 | Fischer et al. |
| 7,175,238 B1 | 2/2007 | Barman |
| 7,181,799 B2 | 2/2007 | Gavney, Jr. et al. |
| 7,185,383 B2 | 3/2007 | Gatzemeyer et al. |
| 7,186,226 B2 | 3/2007 | Woolley |
| D540,542 S | 4/2007 | Harada |
| 7,198,487 B2 | 4/2007 | Luettgen et al. |
| 7,207,080 B2 | 4/2007 | Hilscher et al. |
| 7,210,184 B2 | 5/2007 | Eliav et al. |
| 7,213,293 B1 | 5/2007 | Schraga |
| 7,213,995 B2 | 5/2007 | Bravo-Loubriel |
| 7,217,332 B2 | 5/2007 | Brown, Jr. et al. |
| 7,222,381 B2 | 5/2007 | Kraemer |
| 7,222,382 B2 | 5/2007 | Choi et al. |
| 7,225,494 B2 | 6/2007 | Chan et al. |
| 7,228,583 B2 | 6/2007 | Chan et al. |
| 7,234,187 B2 | 6/2007 | Blaustein et al. |
| 7,234,192 B2 | 6/2007 | Barbar |
| 7,469,440 B2 | 12/2008 | Boland et al. |
| 7,554,225 B2 | 6/2009 | Kraus et al. |
| 7,732,952 B1 | 6/2010 | Taylor |
| 7,857,623 B2 | 12/2010 | Grez |
| 8,032,964 B2 | 10/2011 | Farrell et al. |
| 8,196,245 B2 | 6/2012 | Schwarz-Hartmann et al. |
| 8,256,979 B2 | 9/2012 | Hilscher et al. |
| 8,453,285 B2 | 6/2013 | Dickie |
| 8,769,758 B2 | 7/2014 | Jungnickel et al. |
| 9,687,329 B2 * | 6/2017 | Lee .................... A46B 15/0008 |
| 2001/0035194 A1 | 11/2001 | Narayanan |
| 2001/0039955 A1 | 11/2001 | Winters et al. |
| 2001/0054563 A1 | 12/2001 | Lang et al. |
| 2002/0017474 A1 | 2/2002 | Blaustein et al. |
| 2002/0029988 A1 | 3/2002 | Blaustein et al. |
| 2002/0032941 A1 | 3/2002 | Blaustein et al. |
| 2002/0039720 A1 | 4/2002 | Marx et al. |
| 2002/0059685 A1 | 5/2002 | Paffrath |
| 2002/0078514 A1 | 6/2002 | Blaustein et al. |
| 2002/0084707 A1 | 7/2002 | Tang |
| 2002/0088068 A1 | 7/2002 | Levy et al. |
| 2002/0090252 A1 | 7/2002 | Hall et al. |
| 2002/0092104 A1 | 7/2002 | Ferber |
| 2002/0095734 A1 | 7/2002 | Wong |
| 2002/0100134 A1 | 8/2002 | Dunn et al. |
| 2002/0106607 A1 | 8/2002 | Horowitz |
| 2002/0137728 A1 | 9/2002 | Montgomery |
| 2002/0138926 A1 | 10/2002 | Brown, Jr. et al. |
| 2002/0152563 A1 | 10/2002 | Sato |
| 2002/0152564 A1 | 10/2002 | Blaustein et al. |
| 2002/0174498 A1 | 11/2002 | Li |
| 2002/0178519 A1 | 12/2002 | Zarlengo |
| 2003/0005544 A1 | 1/2003 | Felix |
| 2003/0033679 A1 | 2/2003 | Fattori et al. |
| 2003/0033680 A1 | 2/2003 | Davies et al. |
| 2003/0041396 A1 | 3/2003 | Dickie |
| 2003/0064348 A1 | 4/2003 | Sokol et al. |
| 2003/0066145 A1 | 4/2003 | Prineppi |
| 2003/0074751 A1 | 4/2003 | Wu |
| 2003/0079305 A1 | 5/2003 | Takahata et al. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0097723 A1 | 5/2003 | Li |
| 2003/0099502 A1 | 5/2003 | Lai |
| 2003/0101526 A1 | 6/2003 | Hilscher |
| 2003/0106565 A1 | 6/2003 | Andrews |
| 2003/0140435 A1 | 7/2003 | Eliav et al. |
| 2003/0140437 A1 | 7/2003 | Eliav et al. |
| 2003/0140937 A1 | 7/2003 | Cook |
| 2003/0150474 A1 | 8/2003 | Doyscher |
| 2003/0154567 A1 | 8/2003 | Drossler et al. |
| 2003/0154568 A1 | 8/2003 | Boland et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182746 A1 | 10/2003 | Fattori et al. |
| 2003/0192139 A1 | 10/2003 | Fattori et al. |
| 2003/0196283 A1 | 10/2003 | Eliav et al. |
| 2003/0196677 A1 | 10/2003 | Wiseman |
| 2003/0213075 A1 | 11/2003 | Hui et al. |
| 2003/0221267 A1 | 12/2003 | Chan |
| 2003/0221269 A1 | 12/2003 | Zhuan |
| 2003/0226223 A1 | 12/2003 | Chan |
| 2004/0010870 A1 | 1/2004 | McNair |
| 2004/0010871 A1 | 1/2004 | Nishinaka et al. |
| 2004/0016068 A1 | 1/2004 | Lee |
| 2004/0016069 A1 | 1/2004 | Lee |
| 2004/0034951 A1 | 2/2004 | Davies et al. |
| 2004/0045106 A1 | 3/2004 | Lam |
| 2004/0045107 A1 | 3/2004 | Egeresi |
| 2004/0049867 A1 | 3/2004 | Hui |
| 2004/0049868 A1 | 3/2004 | Ng |
| 2004/0060137 A1 | 4/2004 | Eliav |
| 2004/0063603 A1 | 4/2004 | Dave et al. |
| 2004/0068811 A1 | 4/2004 | Fulop et al. |
| 2004/0074026 A1 | 4/2004 | Blaustein et al. |
| 2004/0083566 A1 | 5/2004 | Blaustein et al. |
| 2004/0087882 A1 | 5/2004 | Roberts et al. |
| 2004/0088806 A1 | 5/2004 | DePuydt et al. |
| 2004/0088807 A1 | 5/2004 | Blaustein et al. |
| 2004/0091834 A1 | 5/2004 | Rizoiu et al. |
| 2004/0107521 A1 | 6/2004 | Chan et al. |
| 2004/0119344 A1 | 6/2004 | Lau et al. |
| 2004/0123409 A1 | 7/2004 | Dickie |
| 2004/0128778 A1 | 7/2004 | Wong |
| 2004/0129296 A1 | 7/2004 | Treacy et al. |
| 2004/0134001 A1 | 7/2004 | Chan |
| 2004/0143917 A1 | 7/2004 | Ek |
| 2004/0154112 A1 | 8/2004 | Braun et al. |
| 2004/0163191 A1 | 8/2004 | Cuffaro et al. |
| 2004/0168269 A1 | 9/2004 | Kunita et al. |
| 2004/0168272 A1 | 9/2004 | Prineppi |
| 2004/0177458 A1 | 9/2004 | Chan et al. |
| 2004/0187889 A1 | 9/2004 | Kemp et al. |
| 2004/0200016 A1 | 10/2004 | Chan et al. |
| 2005/0004498 A1 | 1/2005 | Klupt |
| 2005/0008986 A1 | 1/2005 | Sokol et al. |
| 2005/0102773 A1 | 5/2005 | Obermann et al. |
| 2005/0144745 A1 | 7/2005 | Russell |
| 2005/0189000 A1 | 9/2005 | Cacka et al. |
| 2005/0255427 A1 | 11/2005 | Shortt et al. |
| 2005/0266376 A1 | 12/2005 | Sokol et al. |
| 2006/0010624 A1 | 1/2006 | Cleland |
| 2006/0078844 A1 | 4/2006 | Goldman et al. |
| 2007/0151051 A1 | 7/2007 | Filsouf |
| 2008/0213731 A1 | 9/2008 | Fishburne |
| 2008/0307591 A1 | 12/2008 | Farrell et al. |
| 2009/0019650 A1 | 1/2009 | Grez et al. |
| 2009/0019651 A1 | 1/2009 | Dickie |
| 2009/0178215 A1 | 7/2009 | Gall |
| 2010/0055634 A1 | 3/2010 | Spaulding et al. |
| 2010/0132139 A1 | 6/2010 | Jungnickel |
| 2010/0186179 A1 | 7/2010 | Miller |
| 2011/0010874 A1 | 1/2011 | Dickie |
| 2011/0041268 A1 | 2/2011 | Iwahori et al. |
| 2011/0047729 A1 | 3/2011 | Iwahori |
| 2011/0083288 A1 | 4/2011 | Kressner |
| 2012/0112566 A1 | 5/2012 | Doll |
| 2012/0192366 A1 | 8/2012 | Cobabe |
| 2012/0198635 A1 | 8/2012 | Hilscher |
| 2012/0216358 A1 | 8/2012 | Kloster |
| 2014/0259469 A1 | 9/2014 | Garrigues |

(56) References Cited

U.S. PATENT DOCUMENTS

| | | | |
|---|---|---|---|
| 2014/0259474 A1 | 9/2014 | Sokol et al. | |
| 2015/0107035 A1 | 4/2015 | Sokol et al. | |
| 2015/0297327 A1 | 10/2015 | Miller | |
| 2015/0327965 A1 | 11/2015 | Garrigues | |
| 2016/0022393 A1* | 1/2016 | Yoshida | A46B 15/0006 15/22.1 |

FOREIGN PATENT DOCUMENTS

| | | |
|---|---|---|
| CN | 201223467 | 4/2009 |
| CN | 102111032 | 6/2011 |
| DE | 243224 | 4/1910 |
| DE | 2019003 | 11/1971 |
| DE | 1766651 | 12/1981 |
| DE | 3431481 | 2/1986 |
| DE | 3512190 | 10/1986 |
| DE | 8626725 | 5/1987 |
| DE | 3736308 | 7/1989 |
| DE | 4142404 | 7/1991 |
| DE | 4003305 | 8/1991 |
| DE | 4223195 | 1/1994 |
| DE | 4223196 | 1/1994 |
| DE | 4226658 | 2/1994 |
| DE | 4226659 | 2/1994 |
| DE | 4241576 | 6/1994 |
| DE | 4309078 | 9/1994 |
| DE | 29715234 | 12/1997 |
| DE | 29919053 | 12/2000 |
| DE | 19961447 | 7/2001 |
| DE | 20319996 | 3/2004 |
| DE | 102006061381 | 6/2008 |
| EP | 0210094 | 1/1987 |
| EP | 0354352 | 2/1990 |
| EP | 0661025 | 7/1995 |
| EP | 0704180 | 4/1996 |
| EP | 0968686 | 1/2000 |
| FR | 429447 | 9/1911 |
| FR | 1171337 | 1/1959 |
| GB | 477799 | 1/1938 |
| GB | 500517 | 2/1939 |
| GB | 838564 | 6/1960 |
| GB | 899618 | 6/1962 |
| GB | 1583558 | 8/1977 |
| GB | 2175494 | 12/1986 |
| GB | 2250428 | 6/1992 |
| JP | 53029847 | 3/1978 |
| JP | 53033753 | 3/1978 |
| JP | 3222905 | 10/1991 |
| SE | 324221 | 5/1970 |
| WO | WO 91/13570 | 9/1991 |
| WO | WO 91/19437 | 12/1991 |
| WO | WO 92/10146 | 6/1992 |
| WO | WO 92/16160 | 10/1992 |
| WO | WO 93/10721 | 6/1993 |
| WO | WO 93/15628 | 8/1993 |
| WO | WO 94/04093 | 3/1994 |
| WO | WO 94/26144 | 11/1994 |
| WO | WO 95/02375 | 1/1995 |
| WO | WO 95/33419 | 12/1995 |
| WO | WO 98/47443 | 10/1998 |
| WO | WO 01/28452 | 4/2001 |
| WO | WO 01/45582 | 6/2001 |
| WO | WO 02/071970 | 9/2002 |
| WO | WO 02/071971 | 9/2002 |
| WO | WO 05/063143 | 7/2005 |
| WO | WO 2006/012974 | 2/2006 |
| WO | WO 2008/070730 | 6/2008 |
| WO | WO 2014/145890 | 9/2014 |
| WO | WO 2014/150418 | 9/2014 |

OTHER PUBLICATIONS

Teledyne Water Pik "Plaque Control 3000" plaque removal instrument (Jul. 1991).

American Dentronics Incorporated "Soniplak" sonic plaque removal system (May 1993).

Teledyne Water Pik "Sensonic" Toothbrush, sales brochure (at least as early as Sep. 1994).

International Search Report and Written Opinion, PCT Application No. PCT/US2012/036092, 7 pages, dated Jul. 10, 2012 (P216207. US.03).

* cited by examiner

LOAD SENSING FOR ORAL DEVICES

CROSS-REFERENCE TO RELATED APPLICATIONS

The present disclosure claims priority to U.S. Provisional Application No. 62/333,679 entitled "Load Sensing for Oral Devices" filed on May 9, 2016, which is hereby incorporated by reference herein in its entirety.

TECHNICAL FIELD

The present disclosure relates to oral health products. More specifically, the present disclosure relates to toothbrush systems.

BACKGROUND

Many people use electronically driven toothbrushes as part of a daily oral health routine. Electronically driven toothbrushes typically rotate or oscillate a brush head include one or more bristle groups. While electronic toothbrushes can provide superior cleaning capabilities as compared to conventional non-powered toothbrushes, many users will exert an additional force on the brush head during cleaning. This user applied force, in addition to the force exerted by the stiffness and electronic movement of the bristles, can damage the gums of a user. Therefore, it is desirable to ensure that the force of the bristles on a user's gums remains below a particular level. However, many conventional electronically driven toothbrushes do not have a way to monitor or change the pressure exerted on a user's gums.

The information included in this Background section of the specification, including any references cited herein and any description or discussion thereof, is included for technical reference purposes only and is not to be regarded subject matter by which the scope of the invention as defined in the claims is to be bound.

SUMMARY

In one embodiment, a toothbrush including a pressure sensing function is disclosed. The toothbrush may include a handle and a brush tip releasably connected to the handle, where the brush tip includes multiple bristles connected thereto and rotatable therewith. The toothbrush may also include a power source, a direct current motor in selective communication with the power source, a drive assembly connected between the brush tip and a drive shaft that converts rotation of the direct current motor into oscillation or rotation of the brush tip, and a control assembly in electrical communication with the power source. During operation of the motor, the control assembly monitors a current draw by the motor to assess the pressure being exerted by the bristles on one or more surfaces of a user's mouth and adjusts a current applied to the direct current motor based on the current draw.

In another embodiment, a toothbrush including a pressure sensing function is disclosed. The toothbrush includes a brush tip comprising a plurality of bristles operably coupled thereto, a motor that actuates the brush tip, the plurality of bristles, or a combination thereof, a power source that provides current to the motor, a sensing module that detects a current provided to the motor, and a motor control coupled to the motor and the sensing module, wherein the motor control dynamically adjusts a current provided to the motor based on the detected current.

In another embodiment, a method of operating a toothbrush is disclosed. The method includes detecting, by a sensing module, a current provided to a motor driving a plurality of bristles on a brush tip, wherein the detected current is proportional to a pressure applied to the plurality of bristles, determining, by a processor, whether the detected current exceeds a threshold current, and providing an alert to a user responsive to determining that the detected current exceeds the threshold.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

Overview

The present disclosure is generally related to a system and method to sense an applied load on a brush tip or bristles. Using this method, a toothbrush can provide an alert to a user to indicate that he or she has exceeded a desired force level and/or may automatically adjust one or more characteristics of the system to reduce the applied force, e.g., reduce the power applied to a motor driving the brush tip.

In one example, a toothbrush including a sensing module is disclosed. The toothbrush includes a direct-current (DC) driven motor, a drive assembly connected to and rotated by the motor, a power assembly for providing power to the motor, and a brush head or bristles connected to the drive assembly and configured to be oscillated or rotated by the drive assembly. In this example, the sensing module may monitor the voltage drop across the motor (e.g., by measuring the current that the motor is pulling from the power source) and use the value to determine the force being applied to a user's gums. In some embodiments, the sensing module may include parameters such as, but not limited to, type of brush tip, bristle stiffness, bristle height, no-load values, and the like. These additional parameters may assist in providing a more accurate reading for the toothbrush.

In a specific embodiment, the sensing module may monitor the voltage across a wire connected to the motor. Additionally or alternatively, the sensing module may monitor the voltage of an activating transistor electrically connected to the motor. The sensing modules may be connected to either or both the positive and negative terminals of the motor.

In some embodiments, the sensing module may analyze the detected values against a predetermined current/force relationship. In one embodiment, a linear slope relationship may be used to determine the force applied to the brush tip based on the current applied to the motor. In this example, as soon as the user applies the bristles of the brush tip to a surface in his or her mouth (e.g., gums, teeth, tongue, etc.), the sensing module tracks the current in real-time to adaptively track the motor load and thus the brush tip load, as it varies. An output to the user or a modification to the motor speed may occur when a detected load change is exceeds a predetermined threshold, e.g., magnitude or change value. In some embodiments, the toothbrush may dynamically calculate a threshold level of pressure for a particular brush, using a current/force relationship, e.g., adaptive learning, and use this threshold to detect when the force may damage a user's gums. This helps to accommodate for changes based on wear on the components, bristles, new brush heads, and the like. If the threshold was based solely on a static level, rather than a dynamic relationship, then the threshold may not compensate for increases/decreases in friction and other changes in the brushes.

Detailed Description

Figure 1:
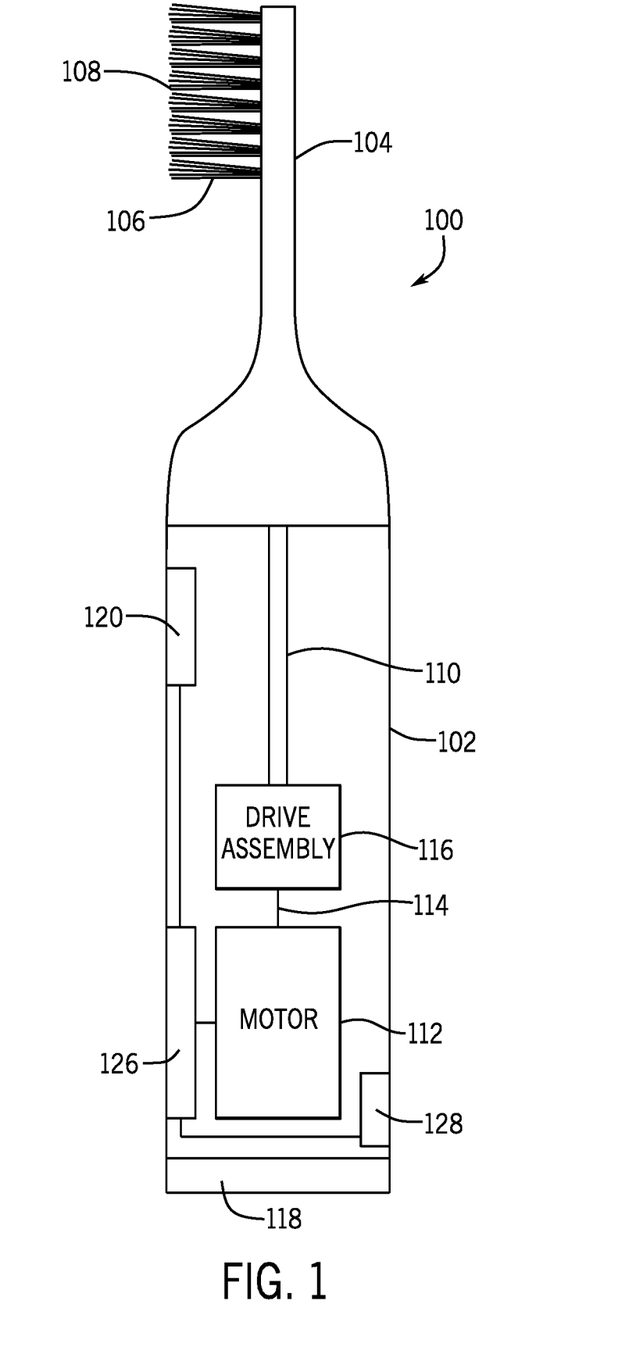
FIG. 1 is a front elevation view of a toothbrush including a load sensing function.
Figure 2:
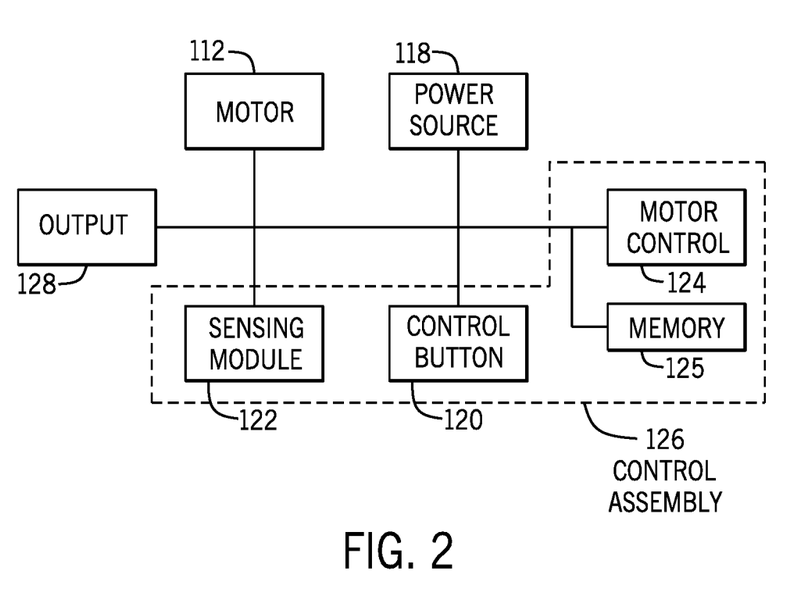
FIG. 2 is a simplified block diagram of the electrically connected components of the toothbrush of FIG. 1.

Turning now to the figures, the method and system will be discussed in more detail below. FIG. 1 illustrates a simplified diagram of a toothbrush of the present disclosure. FIG. 2 is a simplified electronic block diagram of the toothbrush of FIG. 1. With reference to FIGS. 1 and 2, the toothbrush 100 may include a handle 102 and a brush tip 104 including a brush head 106 having a plurality of bristles 108 connected thereto. The brush tip 104 is driven by an output shaft 110 connected to a drive assembly 116, which is connected via a drive shaft 114 to a motor 112. The motor 112 is powered by a power source 118 and is controlled by a control assembly 126 that may include user inputs through one or more control buttons 120. Each of the components will be discussed, in turn, below.

The handle 102 defines a main body of the toothbrush 100 and acts to house the various internal components (e.g., motor 112, drive assembly 116, etc.). In many embodiments the handle 102 may be formed by two shells that are connected together to define an internal cavity. However, in other embodiments the handle 102 may be differently configured. In some embodiments the toothbrush 100 may also include a washing or irrigating function and in these embodiments the handle 102 may include a fluid connection to a reservoir or the like, as well as one or more fluid pathways defined therein or connected thereto, that transfer fluid from the reservoir to the brush tip 104.

The brush head 104 is movable relative to the handle 102 and may be removably connected to a top end of the handle 102. The brush tip 104 is connected to the output shaft 110 which drives the brush head 104 in an oscillating motion (e.g., back and forth about a pivot point) or to drive the brush head 106 in a rotational movement relative to the handle 102. The brush tip 104 includes a plurality of bristles 108 that are connected to the brush head 106. The bristles 108 may be uniform or may have varying heights, stiffness, and/or materials in order to provide a desired output characteristic. As will be discussed in more detail below, in some embodiments various characteristics of the bristles 108 may be provided as an input or otherwise adjusted for by the toothbrush 100 when determining a desired motor 112 speed. For example, the stiffer the bristles 108 the slower the motor 112 may need to rotate to achieve a desired exertion force on a user's teeth and gums. It should be noted that in some embodiments, the entire brush head 104 may move in order to move the bristles 108 correspondingly. In other examples, the brush head 104 may connect to a bristle head or carrier that supports the bristles. In these examples, the bristle carrier only may move and the brush head may remain stationary.

The motor 112 is used to drive the brush tip 104 and/or brush head 106. In many embodiments the motor 112 is a high speed DC motor that, when activated, rotates the drive shaft 114 in a continuous manner. In some embodiments, the drive shaft 114 may be an eccentric shaft having one portion aligned with a center axis of the motor 112 and one portion offset from the center axis of the motor 112. In other embodiments, the drive shaft 114 may be straight and be aligned with the center axis of the motor 112. In some embodiments, the motor will rotate between 5500 to 16000 rpms depending on whether sonic or sub-sonic rotary motion is desired. In one example, a DC motor having a maximum efficiency load of 6900 rpms, a no-load speed of 8300 rpm, and a loaded speed of 5500 rpms may be used. However, in other embodiments, other speeds may be used and may vary depending on the desired output characteristics of the toothbrush 100. For example, using a direct drive assembly 116, the motor 112 may operate at higher speeds, such as 16000 rpms. In some embodiments, the motor 112 may operate with a voltage range between 2.4 to 8.7 Volts. However, in other embodiments other voltage ranges may be used.

The drive assembly 116 converts rotation of the drive shaft 114 into a desired output motion of the brush tip 104 and/or brush head 106. For example, the drive assembly 116 may convert the rotational movement of the drive shaft 114 into an oscillating movement of the brush tip 104. In another embodiment, the drive assembly 116 may transfer rotary motion of the drive shaft 114 into rotational movement of the brush head 106 relative to the brush tip 104. The drive assembly 116 may be a direct drive configuration or may be an indirect configuration (e.g., gear reduction or the like). Additionally, the drive assembly 116 may reduce the speed of the movement as compared to the rotational speed of the drive shaft 114. Examples of drive assemblies 116 that may be used with the toothbrush 100 may be found in U.S. patent application Ser. No. 13/833,897 entitled "Electronic Toothbrush with Vibration Dampening," filed on Mar. 15, 2013, U.S. Pat. No. 8,943,634 entitled "Mechanically-Driven, Sonic Toothbrush System," filed on May 2, 2012, U.S. patent application Ser. No. 14/216,779 entitled "Mechanically-Driven, Sonic Toothbrush and Water Flosser" filed on Mar. 17, 2014, and U.S. Provisional Application No. 62/190,094 entitled "Irrigating Toothbrush" filed on Jul. 8, 2015, each of which are hereby incorporated by reference in their entireties.

The output shaft 110 is connected to the drive assembly 116 and may include two or more shafts connected together. The output shaft 110 may be inserted into a cavity in the brush tip 104 to drive the motion of the brush tip 104 or may connect to an internal shaft within the brush tip 104.

The power source 118 provides power to the motor 112, as well as other components of the toothbrush 100 that may require power (e.g., control assembly 126, output elements 128, lights, or the like). In some embodiments the power source 118 may be a battery (either rechargeable or replaceable), in other embodiments the power source 118 may be a power cord or the like that connects to an external power source (e.g., wall outlet).

The control buttons 120 allow a user to provide input to control the operation of the motor 112. For example, the control buttons 120 may include a power button to allow a user to activate the motor 112. Additionally the control buttons 120 may include a speed or setting button that allows a user to increase or decrease the speed of the motor 112. In embodiments where the toothbrush 100 may have additional functions (e.g., irrigating function), the control buttons 120 may also change the functionality of the toothbrush 100, such as activating the fluid flow.

With reference to FIG. 2, the control assembly 126 will be discussed in more detail. The control assembly 126 is electronically connected to the motor 112, the power source 118, the control buttons 120, and one or more output elements 128 (e.g., light emitting diodes, speaker, vibrating motor, or the like). The control assembly 126 controls operation of the motor 112 and thus the output characteristics of the brush tip 104 and bristles 108. The control assembly 126 may include a motor control 124 that may include one or more processing elements (e.g., microprocessors) that vary the input signals to the motor 112 to provide a desired output, such as by providing a higher or lower voltage or a pulse width modulated signal. The control assembly 126 may also include one or more sensing modules 122 that directly or indirectly measure the force applied to the bristles 108 and one or more memory components 125 that store pressure thresholds and/or brush tip 104 characteristics.

The sensing module 122 provides feedback to the motor control 124 regarding the operation of the brush tip 104 and can be used to automatically vary the output of the motor 112 or to activate the output element 128. In one embodiment, the sensing module 122 tracks the mechanical load experienced on the bristles 108 by tracking the current applied to the motor 112. In one example, the sensing module 122 may be an in-series current sense that monitors the voltage across the motor wire connections (e.g., in the connection wire before or after the motor 112, such as the connection wires on the positive and negative side of the motor 112). For example, the current sense may include a current sensor (such as an ammeter), a voltage meter, or any other type of device capable of measuring, directly or indirectly, an electrical current. As another example, the sensing module 122 may be a motor-control sense that monitors the voltage of a control switch, such as a transistor (e.g., field effect transistor (FET)), using the inherent resistance during the on-state of the transistor (e.g., drain-source on resistance ($R_{DS(on)}$)). As yet another example, the sensing module 122 may include using a sensing resistor positioned in series with the motor 112 or to add additional lengths of wire traces to a circuit board including the various components. However, with the sensing resistor option, a drop in efficiency may occur due to the introduced loss through the resistor and therefore may not be desired in some configurations.

Figure 3:
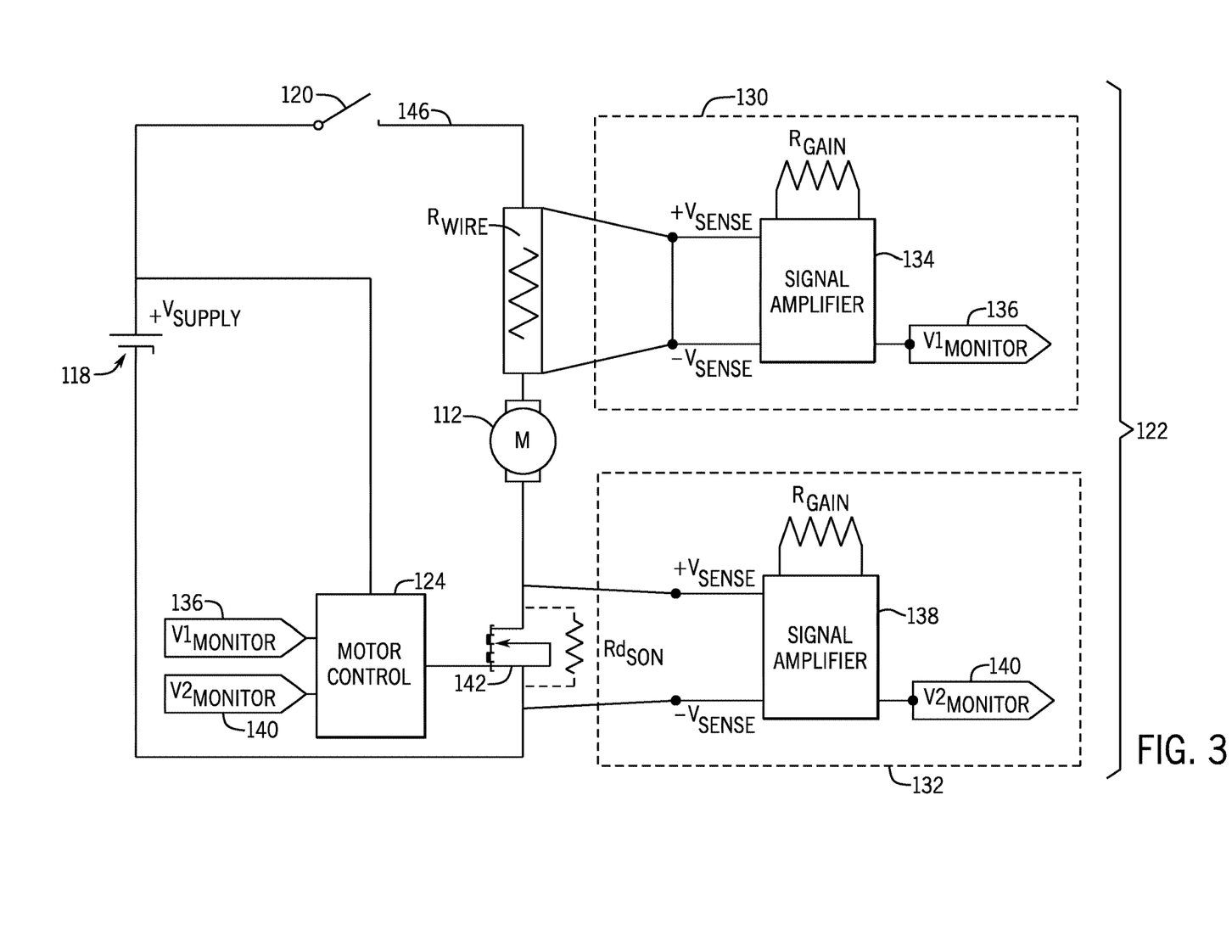
FIG. 3 is a wiring diagram of a feedback loop for sensing the pressure applied to the bristles of the toothbrush.

FIG. 3 illustrates an exemplary wiring diagram for the toothbrush 100. With reference to FIG. 3, in this embodiment, the sensing module 122 includes a positive sensing module 130 and a negative sensing module 132 which together form a feedback loop for the motor 112 operation. The positive sensing module 130 is positioned on the positive or high side of the motor 112, e.g., electrically connected to the positive terminal of the power source 118. The negative sensing module 132 is connected to the negative or low side of the motor 112, e.g., electrically connected to the negative terminal of the power source 118 and motor 112. Either or both sensing modules 130, 132 may be used to sense the current to the motor 112 and thus allow the motor control 124 to determine the load on the motor 112 and adjust accordingly and/or provide an alert or other output to the user.

In one embodiment, the positive sensing module 130 is an in-series current sense that monitors the voltage across the wire or trace connection 146 from the power source 118 to the positive terminal of the motor 112. In this example, the positive sensing module 130 may include a signal amplifier 134 that amplifies the detected signal before generating a first voltage output 136. As noted above, in other embodiments, the positive sensing module 130 may be differently configured and may be a current sense, rather than a voltage reference as shown point in FIG. 3.

With continued reference to FIG. 3, in this embodiment, the negative sensing module 132 may be a transistor or control sense. In this example, the negative sensing module 132 may monitor the voltage across a transistor 142, which may be a FET, using the drain-source resistance $R_{DS(on)}$ when the transistor 142 is in the on-state (e.g., allowing current to flow through the channel) and the motor 112 is operating. As with the positive sensing module 130, the negative sensing module 132 may include a signal amplifier 138 that amplifies the detected signal before generating a second voltage output 140. That is, the sensing module senses amplified voltages to monitor levels allowing operational closed loop feedback control.

As shown in FIG. 3, the voltage outputs 136, 140 may be supplied as inputs to the motor control 124. As will be discussed in more detail below, these inputs allow the toothbrush 100, and in particular, the motor control 124 to alert a user through the output elements 128 when the applied force exceeds a particular threshold and/or adjust the operation of the motor 112 accordingly.

Operation of the toothbrush 100 will now be discussed. With reference to FIGS. 1 and 2, when a user provides an input to the control buttons 120, a switch is closed to electrically connect the motor 112 to the power source 118. In some embodiments, the voltage level provided to the motor 112 is selected by the motor control 124. When powered, the motor 112 begins to operate, rotating the drive shaft 114. Rotation of the drive shaft 114 generates motion in the drive assembly 116 which converts the motion profile into a desired output movement. The output shaft 110, which is connected to the brush tip 104 moves the brush tip 104 in an oscillating or rotational manner, to move the bristles 108. In some embodiments the brush tip 104 may be rotated at a sonic speed to enhance cleaning.

As the user presses the bristles 108 against surfaces in his or her mouth, the added pressure provides a counteracting force on the motor causing the load on the motor 112 to increase. In particular, the harder the user presses the bristles 108 against a surface, the more torque the motor 112 may require in order to continue to rotate the bristles 108 at the desired or selected speed. In this manner, the current drawn by the motor 112 is proportional to the load (e.g., the force required to move the bristles 108), and as the load increases the current drawn by the motor 112 also increases.

Figure 4:
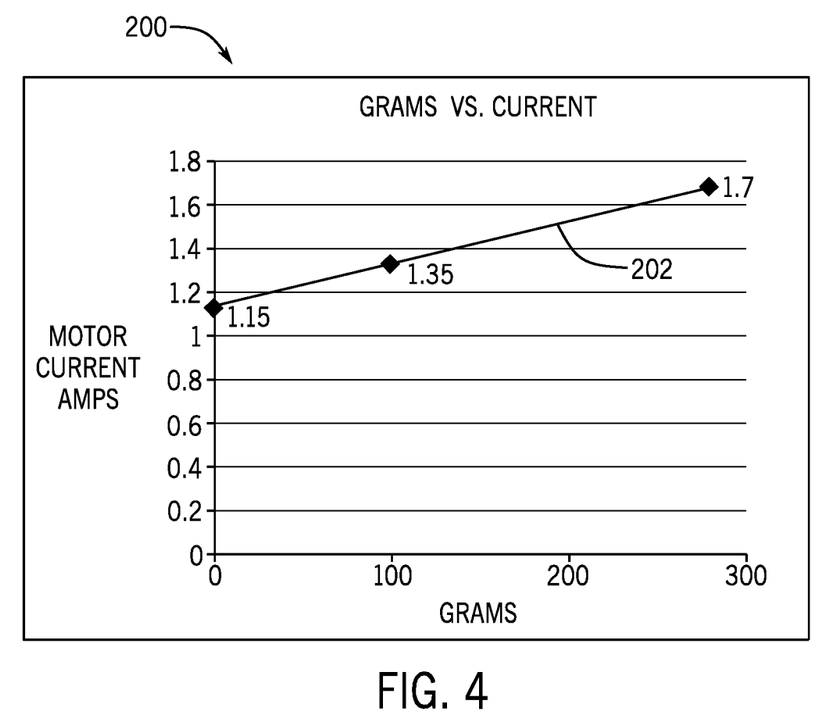
FIG. 4 is a graph illustrating a relationship between motor current and pressure that can be used to adjust operation of the toothbrush.

By analyzing the motor current, along with other factors, such as characteristics of the brush tip 104, bristles 108 (e.g., strand thickness, tuft height (or heights when the brush head has groups of bristles with different heights), tuft counts, and the like), drive assembly 116, a relationship between the pressure exerted onto the applied surface as compared to the current drawn by the motor can be determined. FIG. 4 illustrates an exemplary graph illustrating a pressure-current relationship for the motor 112, where the pressure is measured in centimeter/gram/second units of g/cm². As shown in FIG. 4, the pressure exerted on the interior surface (e.g., gums) of a user is related to the current drawn (in amps) by the motor 112 in a linear relationship 202. Using this relationship 202, the toothbrush 100, in particular, a processing element in the motor control 124, can determine or estimate the pressure being applied by the bristles 108 by monitoring the current of the motor 112. Specifically, the processing element may extrapolate an estimated pressure based on the detected current. The detected current may be from one or both sensing modules 130, 132.

Figure 5:
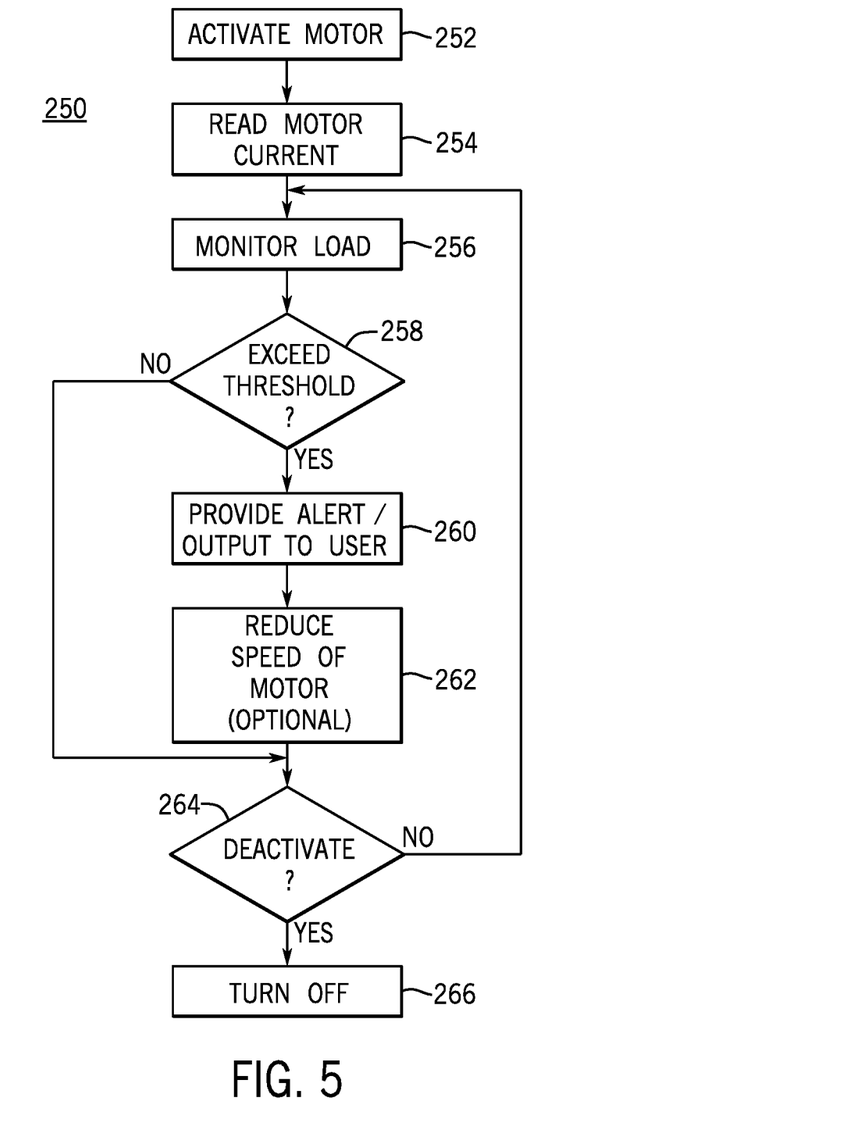
FIG. 5 is a flow chart illustrating a method for using the pressure-current relationship of FIG. 4 and the feedback loop of FIG. 3 to adjust operation of the toothbrush of FIG. 1.

A method for using the pressure-current relationship 202 of FIG. 4 to adjust operation of the toothbrush 100 will now be discussed. FIG. 5 is a flow chart illustrating a method 250 for adjusting the operation of the toothbrush 100. With reference to FIG. 5, the method 250 may begin with operation 252 and the motor 112 is activated. For example, the use may activate one of the control buttons 120 which closes a connection between the power source 118 and the motor 112, providing voltage to the motor 112. As the motor 112 is activated, the method 250 proceeds to operation 254 and the control assembly 126 determines the current draw by the motor 112 shortly after start up. In particular, using the sensing module 122 (e.g., positive sensing module 130 and/or negative sensing module 132) the control assembly 126 (e.g., a processing element in the motor control 124) determines the current being drawn to the motor 112 by assessing the voltage drop across the motor and various sensing points in the control system 112, 146, 130, 132, 142. Operation 254 may be done just after start-up, since the initial current to start the motor may be higher than the no-load current. For example, the initial calibration may be performed within 50 ms of motor activation.

Operation 254 uses the motor current as the motor 112 is first activated to determine the no-load condition of the motor 112. In particular, as soon as the user activates the toothbrush 100, the system assumes that he or she has not yet positioned the bristles 108 against surfaces in his or her mouth, or if the user has positioned the bristles 108 against a surface, the pressure exerted manually by a user is very light. By creating an initial reading during operation 254, the method 250 can create a baseline value and account for variations in the toothbrush 100 over time. For example, normal operation may cause the drive assembly 116 and output shaft 110 to wear-in, reducing the friction on the motor 112 and thus reducing the no-load conditions on the motor 112. As another example, as a user's bristles 108 wear due to use or if the user replaces the brush tip 104 with a different type of brush tip or with stiffer bristles 108, the method 250 can accommodate for those changes. As yet another example, factory calibration conditions may not account for manufacturing tolerances and the specific characteristics of each toothbrush 100.

In some embodiments, the method 250 may include determining a baseline or expected pressure range during operation 254. For example, some users may place the bristles 108 against their teeth with some force before turning on the toothbrush 100. In this example, the initial detected condition may not be a true no-load and the system may not accurately detect when the actual exerted pressure exceeds the predetermined pressure thresholds since the initial baseline reading is incorrect. Accordingly, in these embodiments, if the initial load is greater than an acceptable no-load condition (which may be a range of values or threshold), a default or historical no-load condition is applied to initialize the readings. The default or historical no-load conditions may be stored, for example, in the memory 125 and accessed by the motor control 124 when needed.

With reference again to FIG. 5, after operation 254, the method 250 may proceed to operation 256. In operation 256, the sensing module 122 continues to monitor the load applied to the motor 112 as the user is using the toothbrush 100. For example, with reference to FIG. 3, the motor control 124 may use the first and second voltage outputs 136, 140 to track the pressure exerted by the user. As the motor control 124 continues to track the pressure, the method 250 may proceed to operation 258. In operation 258, the motor control 124, e.g., a processing element, determines whether the pressure exerted by the bristles 108 on a surface exceeds a predetermined threshold.

In particular, the motor control 124 may determine the current being drawn by the motor 112 by evaluating the first voltage output 136 and/or the second voltage output 140. In some embodiments only the change in current between the initial value as determined in operation 254 and the value determined in operation 256 may be evaluated, rather than the full current value. In some embodiments, signal processing is applied in the control assembly 126 based on singular or sampling average techniques allowing accurate/stable current readings.

Using the voltage drop across the motor to determine the current used by the motor 112, the motor control 124 or other processor refers a pressure-current relationship, such as the linear pressure-current relationship shown in FIG. 4 to assess the output pressure by the bristles 108. In particular, the slope of the line 202 in FIG. 4 is used to predict the output pressure by providing an input of the current. In some embodiments, the threshold may be a pressure value. In other embodiments, the threshold may be a current change (e.g., current delta) from a no-load or normal-load current value. The type of threshold may vary as desired. In some embodiments, the current value corresponding to a particular pressure value may vary, but the delta between a baseline or no-load condition and a pressure threshold may remain constant across various motors. Thus, in some embodiments, using a delta value, rather than an absolute magnitude may allow multiple types of motors to be analyzed.

The threshold value may be stored in a memory component 125 in the motor control 124 or in the control assembly 126 and may be selected based on characteristics of the brush tip 104, bristles 108, drive assembly 116, or the like. In some embodiments, the pressure threshold may be between around 280 to 430 grams (e.g., 10 to 15 ounces). This pressure range has been found to be sufficient to prevent damage to a user's gums, while still allowing effective cleaning and plaque removal. However, in other embodiments, different pressure thresholds may be selected. For example, depending on the stiffness of the bristles 108 the threshold may increase or decrease. In particular, for very stiff bristles 108, the threshold may reduce to about 140 grams (e.g., 5 ounces). In some embodiments, the toothbrush may include inputs that allow a user to provide information regarding the characteristics of the brush tip 104 or user preferences which can be used to set or adjust the pressure threshold.

If in operation 258, the pressure exceeds the threshold, the method 252 may proceed to operation 260. In operation 260, the control assembly 126 may provide an output to the user. For example, the output element 128 may be activated to vibrate the brush handle 102, turn on one or more lights, turn the motor 112 off, produce a buzz or other audible sound, create a stutter motion by the brush tip 104, or the like.

The method 252 may also include operation 262. In operation 262, if the pressure exceeds the predetermined threshold, the motor control 124 may reduce the speed of the motor 112. For example, the motor control 124 may reduce the current or voltage applied to the motor 124, which in turn will reduce the rotational speed of the drive shaft 114. The motor control 124 may adjust the voltage in various manners, but in one embodiment, the motor control 124 may include the transistor 142 which can be modulated (e.g., by modulating a gate condition or a channel condition of the transistor 142) to vary the motor speed. In other examples, a rheostat, signal generator, or other components can be used to provide varying voltage magnitudes to the motor 112. As yet another example, in one embodiment, a FET is driven in ohmic mode in combination with a digital potentiometer assembled as an extension of the motor control transistor 142.

After operation 262 or if in operation 258 the pressure did not exceed the threshold, the method 250 may proceed to operation 264. In operation 264, the motor control 124 determines whether the motor 112 should be deactivated. For example, the motor control 124 may determine whether the control button 120 for powering off the toothbrush 100 has been activated by a user. As another example, the toothbrush 100 may operate the motor 112 for a predetermined amount of time and automatically deactivated the motor 112 when the time expires. If the motor 112 is to be deactivated, the method 252 proceeds to operation 266 and the power source 118 is disconnected from the motor 112 to deactivate the motor 112. However, if the motor 112 is not to be deactivated, the method 252 may return to operation 256 and continue to monitor the pressure.

Using the method 250, the toothbrush 100 can provide adaptive pressure sensing for the DC motor 112, and help to prevent users from exerting too much pressure on interior surfaces in their mouths. The adaptive pressure sensing adjusts to accommodate mechanical and functional changes to the toothbrush, which is not possible with conventional toothbrushes. In some embodiments, the method 250 may track, using the sensing module 122, deltas or changes in current of a motor and uses these data points to adjust operation of the motor 112 or toothbrush 100. For example, the processing element may track a delta change from an operating or no-load current draw by the motor 112. In particular, in some instances a user's force may generate a consistent change in current (as compared to a current magnitude) by the motor 112 (e.g., an ampere change between 400 to 650 milliamps).

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A toothbrush comprising:
   a handle;
   a brush tip connected to the handle, wherein the brush tip includes a plurality of bristles operably connected thereto;
   a power source;
   a direct current motor in selective electrical communication with the power source, wherein the motor includes a drive shaft;
   a drive assembly connected between the brush tip and the drive shaft, wherein the drive assembly converts rotation of the drive shaft into movement of the plurality of bristles; and
   a control assembly in electrical communication with the motor and the power source; wherein
   after activation of the motor, the control assembly determines an initial current draw by the motor to determine a no-load condition of the motor; and
   once the initial current draw is determined and the motor continues to operate, the control assembly monitors an operating current draw by the motor and adjusts a current applied to the direct current motor based on comparison of a delta between the initial current draw and the operating current draw to a predetermined threshold.

2. The toothbrush of claim 1, further comprising an output element in communication with the control assembly.

3. The toothbrush of claim 2, wherein when the delta between the initial current draw and the operating current draw exceeds the predetermined threshold, the output element provides an output to the user.

4. The toothbrush of claim 1, wherein the control assembly comprises one or more sensing modules that detect a current provided to the direct drive motor.

5. The toothbrush of claim 4, further comprising a field effect transistor coupled to the control assembly and the direct drive motor that modulates the current provided to the direct drive motor based on the detected current.

6. A toothbrush comprising:
   a brush tip comprising a plurality of bristles operably coupled thereto;
   a driver that actuates movement of the brush tip, the plurality of bristles, or a combination thereof;
   a power source that provides current to the driver;
   a sensing module that detects an initial current provided to the driver within a no-load window after startup and that detects an operating current provided to the driver during normal operation; and
   a controller coupled to the driver and the sensing module, wherein the controller dynamically adjusts a provided current to the driver based on a comparison of a delta between the initial current provided to the driver within the no-load window and the operating current provided to the driver during normal operation to a predetermined current threshold, wherein the comparison determines an adjustment to the current provided to the driver.

7. The toothbrush of claim 6, wherein the detected current is proportional to a pressure applied to the plurality of bristles.

8. The toothbrush of claim 6, further comprising a transistor coupled between the power source and the motor, wherein the sensing module comprises a signal amplifier that detects a drain-source voltage of the transistor.

9. The toothbrush of claim 8, wherein the controller adjusts the provided current to the driver by dynamically adjusting a gate condition or a channel condition of the transistor.

10. The toothbrush of claim 6, wherein the controller provides an alert to a user responsive to the delta exceeding the current threshold.

11. A method of operating a toothbrush comprising:
determining an initial current provided to a motor driving a plurality of bristles on a brush tip wherein the initial current is determined prior to applying any pressure to the plurality of bristles;
detecting, by a sensing module, a current provided to the motor, wherein the detected current is proportional to a pressure applied to the plurality of bristles and the detected current is determined relative to the initial current;
determining, by a processor, a delta between the detected current and the initial current;
determining, by the processor, whether the delta exceeds a threshold current; and
responsive to determining that the delta exceeds the threshold current, providing an alert to a user responsive to determining that the delta exceeds the threshold or dynamically adjusting one of a current or a voltage provided to the motor.

12. The method of claim 11, wherein the initial current is determined within 50 ms of activating the motor.

13. The method of claim 11, wherein dynamically adjusting the current or the voltage provided to the motor comprises adjusting a rheostat coupled between a power source and the motor.

14. The method of claim 11, wherein dynamically adjusting one of a current or a voltage provided to the motor comprises modulating a transistor coupled between the motor and a power source providing current to the motor.

15. The method of claim 14, wherein detecting the current provided to the motor comprises amplifying a signal detected across the transistor to provide an output signal to the processor.

16. The method of claim 11, wherein dynamically adjusting one of the current or the voltage provided to the motor further comprises reducing the one of the current or the voltage provided to the motor.

17. The method of claim 16, wherein reducing the one of the current or the voltage provided to the motor further reduces the pressure applied to the plurality of bristles.

18. The method of claim 11, wherein the motor includes a drive shaft operably coupled to the brush tip to translation motion of the drive shaft into movement of the brush tip.

19. The method of claim 11, wherein determining that the delta exceeds a threshold current comprises comparing the delta to a linear pressure-current relationship for the motor.

20. The method of claim 19, wherein the linear relationship takes into account one or more of the following: bristle strand thickness, tuft height, or tuft counts.

* * * * *